United States Patent [19]

Hagedorn et al.

[11] 4,424,360

[45] Jan. 3, 1984

[54] PROCESS FOR THE PREPARATION OF FUSED 1,2,3-TRIAZOLES

[75] Inventors: Ferdinand Hagedorn, Leverkusen; Werner Evertz, Monheim, both of Fed. Rep. of Germany

[73] Assignee: Bayer Aktiengesellschaft, Leverkusen, Fed. Rep. of Germany

[21] Appl. No.: 361,693

[22] Filed: Mar. 25, 1982

[30] Foreign Application Priority Data

Apr. 14, 1981 [DE] Fed. Rep. of Germany ....... 3115070

[51] Int. Cl.$^3$ .......................................... C07D 249/16
[52] U.S. Cl. ..................................... 548/257; 548/260
[58] Field of Search ................................ 548/257, 260

[56] References Cited

U.S. PATENT DOCUMENTS 4,146,500  3/1979  Fletcher et al. ..................... 544/310
4,158,660  6/1979  Gavin et al. ......................... 548/257

FOREIGN PATENT DOCUMENTS 1581407  12/1980  United Kingdom ................ 548/257

OTHER PUBLICATIONS

Weda et al., "Synthesis Aromatic Polyamides . . . ", Chem. Abst. 91:5494c 1979.
Saborskii et al., "Anion Exchangers . . . ," Chem. Abst, 84:75053n (1976).

Primary Examiner—Donald G. Daus
Assistant Examiner—G. M. Hendricks
Attorney, Agent, or Firm—Sprung, Horn, Kramer & Woods

[57] ABSTRACT

An improved process for the preparation of fused 1,2,3-triazoles by reaction of an ortho-diaminoaryl with an ester of nitrous acid in a soluent or diluent is disclosed wherein the process is catalyzed by the use of a 1,2,3-triazole.

20 Claims, No Drawings

PROCESS FOR THE PREPARATION OF FUSED 1,2,3-TRIAZOLES

The invention relates to a process for the preparation of fused 1,2,3-triazoles by the reaction of aromatic diamino compounds with an ester of nitrous acid.

The preparation of fused triazoles by the reaction of an o-diamine from the series comprising the aromatic 6-membered rings with an alkyl nitrite, in the presence of a mineral acid or a carboxylic acid as the catalyst, in an organic solvent is known from German Offenlegungsschrift No. 2,822,506. After the end of the reaction, the acids employed as catalysts have to be neutralized and separated off.

A process for the preparation of fused 1,2,3-triazoles by the reaction of ortho-diaminoaryls with an ester of nitrous acid in a solvent or diluent has now been found, which is characterized in that the 1,2,3-triazole to be prepared is added as the catalyst.

1,2,3-Triazoles of the formula

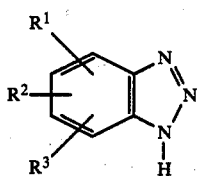

wherein
R$^1$, R$^2$ and R$^3$ are identical or different and denote hydrogen, alkyl, aryl, aralkyl, halogen, alkoxy or nitro, and wherein two adjacent hydrocarbon radicals can be bonded to form an aromatic 5-membered or 6-membered ring, may be mentioned as reaction products of the process according to the invention, which are employed, according to the invention, as catalysts.

According to the invention, alkyl can be a straight-chain or branched hydrocarbon radical having 1 to 12 carbon atoms. Lower alkyl having 1 to about 6 carbon atoms is a preferred alkyl. The following alkyl radicals may be mentioned as examples: methyl, ethyl, propyl, isopropyl, butyl, isobutyl, pentyl, isopentyl, hexyl and isohexyl.

According to the invention, aryl can be an aromatic hydrocarbon radical having 6 to 12 carbon atoms. The phenyl radical is a preferred aryl.

According to the invention, aralkyl, in the aliphatic part, can be a straight-chain or branched hydrocarbon radical having 1 to 6 carbon atoms and, in the aromatic part, can be an aromatic hydrocarbon radical, preferably the phenyl radical or naphthyl radical. The benzyl radical and the α- or β-methylene-naphthyl radical are preferred aralkyl radicals.

According to the invention, halogen can be fluorine, chlorine, bromine or iodine, preferably chlorine or bromine.

According to the invention, alkoxy, in the aliphatic part, can be a straight-chain or branched, aliphatic hydrocarbon radical having 1 to 12 carbon atoms. The lower alkoxy radical having 1 to about 6 carbon atoms is a preferred alkoxy. The following alkoxy radicals may be mentioned as examples: methoxy, ethoxy, propoxy, isopropoxy, butoxy, isobutoxy, pentoxy, isopentoxy, hexoxy and isohexoxy.

Compounds of the formula (II)

wherein
R$^4$ and R$^5$ are identical or different and denote hydrogen, lower alkyl, phenyl, chlorine, bromine, lower alkoxy or nitro, are preferred 1,2,3-triazoles.

The following 1,2,3-triazoles may be mentioned as examples: benzotriazole, 5-methyl-benzotriazole, 4-methylbenzotriazole, mixtures of 5- and 4-methylbenzotriazole, mixtures of benzotriazole and methyl-benzotriazoles, 1,2-naphthotriazole and 2,3-naphthotriazole.

In general, the 1,2,3-triazole is employed as a catalyst for the process according to the invention in a quantity of from 0.001 to 0.5 mol, preferably 0.01 to 0.1 mol, per mol of the ortho-diaminoaryl.

Ortho-diaminoaryls for the process according to the invention can, for example, be compounds of the formula (III)

wherein R$^1$, R$^2$ and R$^3$ have the abovementioned meaning.

Preferred ortho-diaminoaryls for the process according to the invention are compounds of the formula (IV)

wherein R$^4$ and R$^5$ have the abovementioned meaning.

The following ortho-diaminoaryls may be mentioned as examples: 1,2-diaminobenzene, 2,3-diamino-toluene, 3,4-diaminotoluene, 1,2-diaminonaphthalene and 2,3-diaminonaphthalene. Preferred ortho-diaminoaryls for the process according to the invention are: 1,2-diaminobenzene, 2,3-diamino-toluene and 3,4-diaminotoluene.

It is, of course, also possible to employ mixtures of the ortho-diaminoaryls. Thus, for example, it is possible advantageously to use an isomer mixture of 2,3- and 3,4-diaminotoluene.

The ortho-diamines to be used according to the invention are in themselves known and can be prepared according to known methods.

Nitrous acid esters for the process according to the invention are, in general, the esters of nitrous acid with primary or secondary alcohols, which esters are customary for diazotization reactions (Houben-Weyl, Volume X/3, pages 28 and 29 (1965)). Esters of nitrous acid with low primary alcohols (1 to about 6 carbon atoms) are preferred for the process according to the invention.

Methyl nitrite, ethyl nitrite, propyl nitrite, isopropyl nitrite, butyl nitrite, isobutyl nitrite, pentyl nitrite, isopentyl nitrite, hexyl nitrite and isohexyl nitrite may be mentioned as examples of nitrous acid esters. Methyl nitrite is preferred for the process according to the invention.

The preparation of the nitrous acid esters is in itself known.

In general, the nitrous acid ester is employed, for the process according to the invention, in a quantity of from 1.0 to 1.2 mol, preferably of from 1.0 to 1.1 mol, per mol of the ortho-diaminoaryl.

The process according to the invention is carried out, in general, in the temperature range of from $-20°$ to $100°$ C., preferably from $20°$ to $80°$ C. The process according to the invention is carried out, in general, under normal pressure. However, it is of course also possible to carry out the process under reduced pressure or elevated pressure.

The process according to the invention is carried out in solvents or diluents which do not change under the reaction conditions. It is possible to employ protic or aprotic solvents for the process according to the invention.

The following may be particularly mentioned: alcohols, glycols, glycol ethers, aromatic hydrocarbons and chlorinated aromatic hydrocarbons. It is also possible for the solvents or diluents for the process according to the invention to contain water in an amount of up to a maximum of 40% in general. Methanol, water-containing methanol, ethanol, isopropanol, toluene, chlorobenzene, o-dichlorobenzene and xylene are preferred solvents or diluents for the process according to the invention.

The process according to the invention can be carried out, for example, as follows:

The fused 1,2,3-triazoles employed as the catalysts are added to the reaction mixture before the beginning of the reaction, for example as such or dissolved in a solvent or in the particular ortho-diaminoaryl to be reacted or in the ortho-diaminoaryl mixture.

The process of the invention can be carried out by introducing 1,2,3-triazole as catalyst, initially to the reaction vessel followed by introduction of the diaminoaryl and/or the nitrous acid ester. Following that the other reactant would be introduced. Such fused 1,2,3-triazole can be added alone to the reaction vessel or in admixture with the solvent or diluent. Similarly, the 1,2,3-triazole can be added to the reaction mixture in admixture with either the diaminoaryl or the nitrous acid ester, in which case thereafter there would be added the other reactant. It is additionally contemplated to introduce the fused 1,2,3-triazole to the reaction vessel, with or without the diluent or solvent, and thereafter add to such catalyst a mixture of diaminoaryl and nitrous acid ester. In short, the 1,2,3-triazole catalyst can be added to the reaction vessel at any time and in any manner prior to commencement of the reaction in admixture with the other reactant solvent or diluent or alone. Similarly, it can be added in aliquots with some of the catalyst being added prior to commencement of the reaction, i.e., to formation of any fused 1,2,3-triazole from the diaminoaryl and nitrous acid ester, followed by addition of a second aliquot of fused 1,2,3-triazole.

The process can be carried out in the presence or absence of other catalysts useful in catalyzing the reaction. It is particularly preferred that the process be carried out in the absence of catalysts other than said fused 1,2,3-triazole.

After the reaction has ended, the fused 1,2,3-triazole can be isolated according to known methods, for example by distillation.

The use of the particular reaction end product as the catalyst for the diazotization/cyclization reaction simplifies the preparation of the fused 1,2,3-triazoles and facilitates their working-up and isolation. Separating-off and eliminating the acids, or salts thereof, which are used as catalysts, which operations are necessary according to the known process, are advantageously absent in the process according to the invention. The fused 1,2,3-triazoles prepared by the process according to the invention can be used as corrosion inhibitors U.S. Pat. No. 2,861,078, German Offenlegungsschrift No. 2,877,188 and German Auslegeschrift No. 1,285,835).

EXAMPLE 1

Gaseous methyl nitrite (prepared from 72 parts by weight of sodium nitrite, 43 parts by volume of water and 45 parts by volume of methanol, and the dropwise addition of a sulphuric acid, prepared from 80 parts by weight of ice and 40 parts by volume of 96% strength concentrated sulphuric acid) is introduced into a suspension of 108.1 parts by weight of o-phenylenediamine and 3 parts by weight of benzotriazole in 400 parts by volume of a xylene isomer mixture, under nitrogen protective gas, during the course of 2 hours at $20°$ to $25°$ C. The mixture is further stirred for 30 minutes and is then heated for 1 hour at $50°$ C., whilst stirring. After the mixture has stood overnight, methanol, water and 120 parts by volume of xylene are distilled off. 370 parts by volume of xylene are added to the mixture, and the crystalline precipitated benzotriazole is filtered off under suction, after solidification. By reusing the mother liquor, benzotriazole is obtained in an almost quantitative yield with a content of 99%.

EXAMPLE 2

Gaseous methyl nitrite is introduced, until the diamine isomer mixture has completely reacted, into a mixture of 351 parts by weight of 2,3- and 3,4-diaminotoluene in the ratio of about 40:60, 500 parts by volume of methanol and 18 parts by weight of an isomer mixture of 4- and 5-methyl-benzotriazole in the ratio of about 40:60, at $45°$ to $50°$ C. whilst stirring and cooling. Towards the end of the reaction, the reaction mixture is heated to the reflux temperature for approximately 40 minutes, and is then freed, in vacuo, from methanol, excess methyl nitrite and water and purified by thin layer distillation.

Yield: 96% of theory.

EXAMPLE 3

Gaseous methyl nitrite (prepared from 72 parts by weight of sodium nitrite, 43 parts by volume of water and 45 parts by volume of methanol and the dropwise addition of a mixture of 80 parts by weight of ice and 40 parts by volume of 96% strength concentrated sulphuric acid) is introduced into a solution of 118 parts by weight of 3,4-diamino-toluene, and 3 parts by weight of 5-methyl-benzotriazole dissolved in 5 parts by volume of methanol, in 250 parts by volume of o-dichlorobenzene, under nitrogen protective gas, during the course of 2 hours at $40°$ to $45°$ C. The mixture is further heated for 1 hour at $40°$ to $45°$ C., and then for 30 minutes at $80°$ to $85°$ C., whilst stirring.

After excess methyl nitrite has been removed and methanol, water and the bulk of the solvent have been distilled off, the residue is stirred under reflux for 15 minutes with 200 parts by volume of cyclohexane, the mixture is cooled, and the crystalline product is filtered off under suction, washed with 100 parts by volume of cyclohexane and dried.

Yield: almost quantitative, content: 99,5% (gas chromatography).

EXAMPLE 4

118 parts by weight of 2,3-diamino-toluene are reacted with methyl nitrite in o-dichlorobenzene according to the instructions of Example 3, 3 parts by weight of 4-methyl-benzotriazole being initially introduced as the catalyst in this case. After the working-up, 129 parts by weight of 99.8% strength 4-methyl-benzotriazole of melting point 149° to 150° C. are obtained.

What is claimed is:

1. In a process for the preparation of a fused 1,2,3-triazole by reaction of an ortho-diaminoaryl with an ester of nitrous acid in a solvent or diluent, the improvement wherein the process is carried out in the presence of a 1,2,3-triazole as catalyst.

2. A process according to claim 1, wherein said 1,2,3-triazole is present in the reaction mixture, prior to reaction, in an amount of 0.001 to 0.5 mol per mol of ortho-diaminoaryl.

3. A process according to claim 1, wherein said fused 1,2,3-triazole employed as catalyst is introduced into the reaction mixture prior to commencement of the reaction.

4. A process according to claim 1, wherein 1,2,3-triazole is introduced into a reaction vessel containing a solvent or diluent and thereafter ortho-diaminoaryl, nitrous acid ester or a mixture thereof are added thereto.

5. A process according to claim 1, wherein fused 1,2,3-triazole in admixture with a solvent or a diluent is added to ortho-diaminoaryl in a reaction vessel and thereafter there is added said ester of nitrous acid.

6. A process according to claim 1, wherein fused 1,2,3-triazole in admixture with a solvent or diluent is added to said ester of nitrous acid in a reaction vessel and thereafter there is added said ortho-diaminoaryl.

7. A process according to claim 1, wherein said fused 1,2,3-triazole is initially introduced into a reaction mixture, thereafter there is introduced said ortho-diaminoaryl followed by addition of said ester of nitrous acid.

8. A process according to claim 1, wherein the process is carried out in the absence of any other catalyst.

9. A process according to claim 1, wherein said ortho-diaminoaryl is o-phenylenediamine.

10. A process according to claim 1, wherein said ortho-diaminoaryl is 3,4-diamino toluene.

11. A process according to claim 1, wherein said ortho-diaminoaryl is 2,3-diamino toluene.

12. A process according to claim 1, wherein said solvent or diluent is an alcohol or a glycol ether.

13. A process according to claim 1, wherein said solvent or diluent comprises methanol.

14. A process according to claim 1, wherein said solvent or diluent comprises a mixture of methanol and water.

15. A process according to claim 1, wherein said 1,2,3-triazole is a fused triazole.

16. A process according to claim 15, wherein said fused triazole is benzotriazole.

17. A process according to claim 15, wherein said fused triazole is a methyl benzotriazole.

18. A process according to claim 17, wherein said methyl benzotriazole is 4-methyl benzotriazole.

19. A process according to claim 17, wherein said methyl benzotriazole is 5-methyl benzotriazole.

20. A process according to claim 1, wherein the reaction mixture consists essentially of said ortho-diaminoaryl, said ester of nitrous acid, said 1,2,3 triazole, and said solvent or diluent.

* * * * *